US011260091B2

(12) United States Patent
Bobbitt et al.

(10) Patent No.: US 11,260,091 B2
(45) Date of Patent: Mar. 1, 2022

(54) RED SEAWEED EXTRACTS, FORMULATIONS AND ANTI-MICROBIAL USES THEREOF

(71) Applicant: OCEANS LTD., St. John's (CA)

(72) Inventors: Judith Bobbitt, St. John's (CA); Ahmed Zein, St. John's (CA)

(73) Assignee: OCEANS LTD., St. John's (CA)

( * ) Notice: Subject to any disclaimer, the term of this patent is extended or adjusted under 35 U.S.C. 154(b) by 119 days.

(21) Appl. No.: 16/621,436

(22) PCT Filed: Jun. 11, 2018

(86) PCT No.: PCT/CA2018/050695
§ 371 (c)(1),
(2) Date: Dec. 11, 2019

(87) PCT Pub. No.: WO2018/227279
PCT Pub. Date: Dec. 20, 2018

(65) Prior Publication Data
US 2020/0188457 A1   Jun. 18, 2020

Related U.S. Application Data

(60) Provisional application No. 62/518,023, filed on Jun. 12, 2017.

(51) Int. Cl.
*A61K 36/04* (2006.01)
*A61P 31/04* (2006.01)
*A61K 9/06* (2006.01)

(52) U.S. Cl.
CPC ............. *A61K 36/04* (2013.01); *A61K 9/06* (2013.01); *A61P 31/04* (2018.01); *A61K 2236/333* (2013.01)

(58) Field of Classification Search
None
See application file for complete search history.

(56) References Cited

FOREIGN PATENT DOCUMENTS

| EP | 0870507 A1 | 10/1998 |
| WO | 2016090494 A1 | 6/2016 |

OTHER PUBLICATIONS

Jebasingh, S. et al. Potential Antibacterial Activity of Selected Green and Red Seaweeds. J of Pharmaceutical and Biomedical Sciences 5(14)1-7, 2011. (Year: 2011).*
Saravanakumar D. et al. Antimycobacterial Activity of the Red Alga *Polysiphonia virgata*. Pharmaceutical Biology46(4)254-260, 2008. (Year: 2008).*
Batey, J. et al. The Galactan Sulphate of the Red Alga Polysiphonia lanosa. Carbohydrate Research 43(1)133-143, Aug. 1975. (Year: 1975).*
Bajpai, V. Antimicrobial bioactive compounds from marine algae: A mini review. Indian Journal of Geo-Marine Sciences. 2016. Vol. 45(9), pp. 1076-1085.
Chandrasekaran, M. et al. Anti-MRSA activity of Brown and Red algae from Gulf of Mannar Coast, South India. International Journal of Life Sciences and Technology. 2014. Vol. 7(4). pp. 22-31.
Choi, J-S. et al. In vitro antibacterial and anti-inflammatory properties of seaweed extracts against acne inducing bacteria, Propionibacterium acnes. J. Environ. Biol. 2011. vol. 32. pp. 313-318.
Flewelling, A. J. et al. Macroalgal Endophytes from the Atlantic Coast of Canada: A Potential Source of Antibiotic Natural Products? Microorganisms. 2013. vol. 1. pp. 175-187.
Horikawa, M. et al. In Vitro Anti-methicillin-resistant *Staphylococcus aureus* Activity Found in Extracts of Marine Algae Indigenous to the Coastline of Japan. The Journal of Antibiotics. 1999. vol. 52 (2). pp. 189-189.
Hornsey, I. S. et al. The Production of Antimicrobial Compounds by British Marine algae. IV. Variation of Antimicrobial Activity with Algal Generation. British Phycological Society. 1985. vol. 20. pp. 21-25.
Lieberman, H. H. et al. Pharmaceutical Dosage Forms: Tablets vol. I. New York 1989. 592 pp. 18 x 26 cms. ISBN 0-8247-8044-2 (Abstract attached).
Osol, A. and Hoover, J. E. Remington's Pharmaceutical Sciences, 15th Edition. 1975 Mack Publishing Co., Easton, PA 18042. 21 x 29 cm.
Shanmughapriya, S. et al. Antimicrobial activity of seaweeds extracts against multiresistant pathogens. Annals of Microbiology. 2008. vol. 58(3). pp. 535-541.
Tan, S P. et al. Development of a novel antimicrobial seaweed extract-based hydrogel wound dressing. International Journal of Pharmaceutics. 2013. vol. 456. pp. 10-20.

* cited by examiner

*Primary Examiner* — Ralph J Gitomer
(74) *Attorney, Agent, or Firm* — Parker Highlander PLLC

(57) ABSTRACT

The present invention provides crude extracts from the red seaweeds: *Polysiphonia lanosa* (PL), *Polysiphonia urceloata* (PU), *Cystoclonium purpureum* (CP) and *Devaleraea ramentacia* (DR), method of preparation and their use for inhibiting the growth of microbial cells, particularly bacteria causing acne, such as *Propionibacterium acnes*, or causing nosocomial infections such as MRSA in humans or MRSP in dogs.

9 Claims, 2 Drawing Sheets

RED SEAWEED EXTRACTS, FORMULATIONS AND ANTI-MICROBIAL USES THEREOF

CROSS-REFERENCE

The present application is a national phase application under 35 U.S.C. § 371 of International Application No. PCT/CA2018/050695, filed Jun. 11, 2018, which claims priority from U.S. patent application No. 62/518,023, filed on Jun. 12, 2017, the content of each of which is hereby incorporated by reference in its entirety.

FIELD OF THE INVENTION

The present invention relates to extracts from a red seaweed chosen from: *Polysiphonia lanosa* (PL) or *Polysiphonia urceloata* (PU), *Cystoclonium purpureum* (CP), *Devaleraea ramentacia* (DR), method of preparation and use for inhibiting the growth of microorganisms such as bacteria.

BACKGROUND OF THE INVENTION

Acne vulgaris is a common cutaneous multifactorial disease spread worldwide and caused by hormonal, microbiological and immunological mechanisms. Acne is characterized by open and closed comedons (blackheads and whiteheads) and inflammatory lesions like papules, pustules and nodules. *Staphylococcus aureus* and *Propionibacterium acnes* are some of the organisms which proliferate rapidly and cause development of acne. The severity of this skin disorder generally increases with age and time. People normally get affected by it with the onset of puberty affecting both physical & psychological levels and therefore may constitute a cause of concern for physicians.

Acne affects all age groups i.e. 85% of teenagers, about 8% in 25-34 years old and 3% in 35-44 years old. Although it is not a life-threatening disease, it is a distressing skin condition which causes significant psychological disability. Moreover, teenagers or young adults often experience the development of scar and scarring may affect up to 95% of the patients having acne.

There is a large and expanding market for over-the-counter (OTC) medications against acne. The estimated annual worldwide expenditure on acne OTC medication is $100 millions. The long-term treatment of the present synthetic drugs comprising antibiotics and chemotherapeutic agents either inhibit excess sebum production, follicular hyperkeratinisation disorders, cytokines, reactive oxygen species and proliferation of *P. acnes* within the follicle. These drugs are applied either topically or taken orally for the treatment of acne.

The therapeutic success in the treatment of acne is highly dependent on the regular application of topical agents over a prolonged period of time. However, the disadvantages associated with the existing topical therapies defeat the purpose of the treatment and make it patient-noncompliant. Currently available treatment for acne is based on antibiotics and retinoids. The use of antibiotics has limitations due to the development of resistance by bacteria and their untoward side effects, such as skin dryness, pruritus, burning sensation, erythema, occasional hyper pigmentation, local irritation and photosensitization reactions. Furthermore, retinoids are highly teratogenic.

Also, extracts from plants and specific compounds obtained from plant sources are often used in cosmetic and pharmaceutical compositions. European Patent Application Publication No. 0 870 507 describes a synergistic antibacterial composition that includes an extract of botanical material and an essential oil. The essential oil is described as having anti-microbial activity, whereas the botanical extract has significantly lower activity, or no anti-microbial activity, when used alone.

Therefore, alternative treatments of acne using natural products should be studied and developed. There is therefore interest in the development of a topical formulation containing natural extracts possessing antibacterial effect to treat acne such as the development of the present invention.

Nosocomial infections are hospital-acquired infections (HAI) or healthcare-acquired infections whose development is favored by a hospital environment, such as one acquired by a patient during a hospital visit or one developing among hospital staff. In the United States, the Centers for Disease Control and Prevention estimated roughly 1.7 million hospital-associated infections, from all types of microorganisms (i.e. bacteria), combined, cause or contribute to 99,000 deaths each year. Nosocomial infections can cause severe pneumonia and infections of the urinary tract, bloodstream and other parts of the body. Many types are difficult to treat with antibiotics, and antibiotic resistance is spreading to Gram-negative bacteria that can infect people outside the hospital.

Methicillin-resistant *Staphylococcus aureus* (MRSA) is responsible for several difficult-to-treat infections in humans. MRSA comprises any strain of *Staphylococcus aureus* that has developed, through resistance to beta-lactam antibiotics, such as the penicillin-types (methicillin, dicloxacillin, oxacillin, etc.) or the cephalosporins. This resistance makes MRSA infection difficult to treat with standard types of antibiotics and thus more dangerous.

MRSA is especially troublesome in hospitals, prisons, and nursing homes, where patients with open wounds, invasive devices, and weakened immune systems are at greater risk of nosocomial infection than the general public. MRSA began as a hospital-acquired infection but has developed to a limited endemic status and is now sometimes community-acquired.

*Staphylococcus intermedius* is a common species of bacteria found in rabbits and is called *Staphylococcus pseudintermedius* when found in dogs. A small percentage of animals may develop skin infections caused by methicillin-resistant-*Staphylococcus* pseudintermedius (MRSP), and this infection is difficult to get rid of, often requiring aggressive topical therapies, or sometimes, euthanasia.

SUMMARY OF THE INVENTION

A main aspect intended to be addressed by the present invention is to provide a novel extract from a red seaweed selected from the group consisting of: *Polysiphonia lanosa* (PL) and *Polysiphonia urceloata* (PU), *Cystoclonium purpureum* (CP), and *Devaleraea ramentacia* (DR).

According to a further aspect, the present invention provides a composition comprising the extract as defined herein, in admixture with a physiologically acceptable excipient.

According to a further aspect of the present invention, there is provided use of the extract as defined herein for inhibiting growth of microbial cells.

According to a further aspect of the present invention, there is provided use of the extract as defined herein for the manufacture of composition for treating a microbial infection in a mammal.

According to a further aspect, the present invention provides use of the composition as defined herein for the treatment of a microbial infection in a mammal. Particularly, the microbial infection is a bacterial infection or an antibiotic-resistant bacterial infection.

According to a further aspect of the use or the method, both as defined above, the bacterial infection may be selected from the group consisting of: *Staphylococcus aureus*, methicillin-resistant *Staphylococcus aureus* (MRSA), *Staphylococcus* pseudintermedius (SP) and methicillin-resistant *Staphylococcus pseudintermedius* (MRSP). Alternatively, the bacterial infection is one that causes acne, such as, for example, *Propionibacterium acnes* or *Staphylococcus epidermidis*.

According to a further aspect, the present invention provides a method for inhibiting a microorganism comprising contacting said cell with a growth-inhibiting concentration of the extract or the composition as defined herein.

According to a further aspect, the present invention provides a method for treating a microbial infection in a mammal comprising administering a growth-inhibiting concentration of the extract of the composition as defined herein to the mammal.

DETAILED DESCRIPTION OF THE INVENTION

ABBREVIATIONS AND DEFINITIONS

Figure 1:
FIG. 1. Photograph of *Polysiphonia lanosa*.

Abbreviations
CP: *Cystoclonium purpureum*; DR: *Devaleraea ramentacia*; PL: *Polysiphonia lanosa*; PU: *Polysiphonia urceloata*.

Definitions

The term "about" as used herein refers to a margin of + or −10% of the number indicated. For sake of precision, the term about when used in conjunction with, for example: 90% means 90%+1-9% i.e. from 81% to 99%. More precisely, the term about refers to + or −5% of the number indicated, where for example: 90% means 90%+1-4.5% i.e. from 86.5% to 94.5%.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used in this specification and claim(s), the words "consisting essentially of" (and any form of consisting essentially of, such as "consist essentially of" and "consists essentially of"), are inclusive or open-ended, but excludes active, functional essential elements of the composition or combination, such that un-recited elements or method steps can only be non-essential or marginal to the invention.

As used in this specification and claim(s), the words "consisting of" (and any form of consisting of, such as "consist of" and "consists of"), are inclusive or closed-ended and exclude any additional, un-recited elements or method steps.

As used herein, the terms "disease" and "disorder" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

"Mammal" includes humans, domestic animals such as farm animals (e.g. swine, cattle, sheep, goats, horses, rabbits), household pets (e.g. cats, dogs, rabbits, hamsters, ferrets), and non-domestic animals such as wildlife and the like.

The term "subject" or "patient" as used herein refers to an animal, preferably a mammal, and most preferably a human who is the recipient of the treatment, observation or experiment.

The term "extract" as used herein means a composition prepared by contacting solvent with seaweed material and recovering the material from the solvent, produced following the procedures of the invention, which demonstrates inhibitory activity against growth of one or more bacterial strain in vitro. In one aspect of the invention, an extract demonstrates inhibitory activity against bacterial infection in vivo. As used herein, the term "extract" means an extract that is: crude, fractionated, sub-fractionated, separated, isolated, enriched or purified without being limited thereto.

The term "isolated" is used herein to indicate that the protein exists in a physical milieu distinct from that in which it occurs in nature. For example, the isolated molecule may be substantially isolated (for example enriched or purified) with respect to the complex cellular milieu in which it naturally occurs, such as in a crude/primary extract or secondary fractions. When the isolated molecule is enriched or purified, the absolute level of purity is not critical and those skilled in the art can readily determine appropriate levels of purity according to the use to which the material is to be put. In some circumstances, the isolated molecule forms part of a composition (for example a more or less crude extract containing many other substances) or buffer system, which may for example contain other components. In other circumstances, the isolated molecule may be purified to essential homogeneity, for example as determined spectrophotometrically, by NMR or by chromatography (for example LC-MS).

The term "primary" or "crude" means compounds or molecules that have not been entirely separated from the components of the original composition in which it was present. Therefore, the terms "separating", "purifying" or "isolating" refers to methods by which one or more components of the biological sample are removed from one or more other components of the sample.

The extracts described herein can be formulated as compositions by formulation with additives such as physiologically-acceptable excipients, physiologically-acceptable carriers, and physiologically-acceptable vehicles, or as cosmetic formulations with additives such as pharmaceutically- and/or dermatologically-acceptable excipients, carriers, and/or vehicles.

As used herein, the term "pharmaceutically-acceptable" refers being useful in preparing a pharmaceutical composition that is generally safe, non-toxic and neither biologically nor otherwise undesirable and includes being useful for veterinary use as well as human pharmaceutical use.

As used herein, the term "dermatologically-acceptable" refers to molecular entities and compositions that are physiologically tolerable when applied topically on the skin and do not typically produce an allergic or similar unwanted reaction, such as redness or swelling and the like, when administered to human. Preferably, as used herein, the term "cosmetically acceptable" means approved by regulatory agency of the federal or state government or listed in the U.S. Pharmacopeia or other generally recognized pharmacopeia for use in animals, and more particularly in humans.

The term "carrier" refers to a diluent, adjuvant, excipient, or vehicle with which the compounds of the present invention may be administered. Sterile water or aqueous saline solutions and aqueous dextrose and glycerol solutions may be employed as carrier, particularly for topical formulations. Suitable cosmetically carriers are described in "Remington's Pharmaceutical Sciences" by E. W. Martin.

DETAILED DESCRIPTION OF PARTICULAR EMBODIMENTS

Seaweeds

The red seaweed used for the extracts of the invention are chosen from: *Polysiphonia lanosa* (PL), *Polysiphonia urceloata* (PU), *Cystoclonium purpureum* (CP) and *Devaleraea ramentacia* (DR).

Particularly, the red seaweed is *Polysiphonia lanosa* (PL).

Alternatively, the red seaweed is *Polysiphonia urceloata* (PU).

Alternatively, the red seaweed is *Cystoclonium purpureum* (CP).

Alternatively, the red seaweed is *Devaleraea ramentacia* (DR).

Solvent Extracts

With the aim of providing an alternative source of antimicrobial molecules, there is provided a crude solvent extract from the red seaweed *Polysiphonia lanosa* (PL).

With the aim of providing an alternative source of antimicrobial molecules, there is provided a crude solvent extract from the red seaweed *Polysiphonia urceloata* (PU).

With the aim of providing an alternative source of antimicrobial molecules, there is provided a crude solvent extract from the red seaweed *Cystoclonium purpureum* (CP).

With the aim of providing an alternative source of antimicrobial molecules, there is provided a crude solvent extract from the red seaweed *Devaleraea ramentacia* (DR).

Particularly, the crude extract is an organic or inorganic solvent extract. More particularly, the extract's solvent is water or alcohol; and even more particularly: aqueous ethanol.

Particularly, the crude extract is an 80% aqueous ethanol extract. More particularly, the crude extract is a previously hexane-defatted extract.

Extract Form

In accordance with a particular embodiment of the present invention, the extract is in dried form or in solution.

Uses and Methods of Treatment

In accordance with an alternative embodiment, the present invention provides the use of the extract as defined herein for inhibiting growth of microbial cells. Particularly, there is provided the use of the extract as defined herein for the manufacture of composition for treating a microbial infection in a mammal.

In accordance with an alternative embodiment of the invention, there is provided the use of the composition as defined herein for the treatment of a microbial infection in a mammal.

In accordance with a particular embodiment, the present invention provides a method of inhibiting a microbial cell growth comprising contacting said cell with a growth-inhibiting concentration of the extract as defined herein or the composition as defined herein.

More particularly, there is provided a method for the treatment of a microbial infection in a mammal comprising administering a growth-inhibiting concentration of the composition as defined herein to said mammal.

In another embodiment of the present disclosure, there is provided a method for the treatment of a skin disorder in a subject in need thereof, wherein the method comprises administering to the subject a therapeutically effective amount of a composition comprising an anti-microbial amount of the extract as defined herein in admixture with a physiologically-acceptable carrier.

In one embodiment, the administering is topical, whereby the treatment is applied to a skin area affected by the bacterial infection. Compositions suitable for the present method are disclosed herein.

Bacterial Infection

According to a further embodiment, the microbial infection is a bacterial infection or an antibiotic-resistant bacterial infection. Particularly, the bacterial infection may be selected from the group consisting of: *Staphylococcus aureus* (SA), methicillin-resistant *Staphylococcus aureus* (MRSA), *Staphylococcus epidermidis*, *Propionibacterium acnes*, *Staphylococcus intermedius* (SI) and methicillin-resistant *Staphylococcus intermedius* (MRSI), *Staphylococcus pseudintermedius* (SP) and methicillin-resistant *Staphylococcus pseudintermedius* (MRSP).

In another embodiment of the present disclosure, there is provided a use or a method for the treatment of *Staphylococcus aureus* (SA) or methicillin-resistant *Staphylococcus aureus* (MRSA) in a mammal, particularly a human, wherein the method comprises administering to the mammal a therapeutically effective amount of a composition comprising comprising/consisting essentially of/consisting of an anti-microbial amount of the extract as defined herein in admixture with a pharmaceutically-acceptable carrier. In one embodiment, the administering is topical, whereby the treatment is applied to a skin area affected by the SA or MRSA infection. Compositions suitable for the present method are disclosed herein.

In a further embodiment of the present disclosure, there is provided use and a method for the treatment of *Staphylococcus pseudointermedius* (SP) or methicillin-resistant SP (MRSP) in a pet, particularly a dog, wherein the method comprises administering to the pet a therapeutically effective amount of a composition comprising comprising/consisting essentially of/consisting of an anti-microbial amount of the extract as defined herein in admixture with a pharmaceutically-acceptable carrier. In one embodiment, the administering is topical, whereby the treatment is applied to a skin area affected by the SP or MRSP infection. Compositions suitable for the present use and method are disclosed herein.

In a further embodiment of the present disclosure, there is provided use and a method for the treatment of *Staphylococcus intermedius* (SI) or methicillin-resistant SI (MRSI) in a farm animal, particularly a rabbit, wherein the method comprises administering to the rabbit a therapeutically effective amount of a composition comprising comprising/consisting essentially of/consisting of an anti-microbial amount of the extract as defined herein in admixture with a pharmaceutically-acceptable carrier. In one embodiment, the administering is topical, whereby the treatment is applied to a skin area affected by the SI or MRSI infection. Compositions suitable for the present use and method are disclosed herein.

In a further embodiment of the present disclosure, there is provided the use of a seaweed extract against *Staphylococcus epidermidis* or *Propionibacterium acnes*, more particularly *Propionibacterium acnes*.

Composition and/or Formulation

In accordance with a particular embodiment of the invention, there is provided a composition comprising comprising/consisting essentially of/consisting of the extract as defined herein, in admixture with a physiologically—(i.e. pharmaceutically or dermatologically) acceptable carrier.

Thus, embodiments of the present disclosure provide for a composition for topical treatment of skin disorders (including acne vulgaris), the composition comprising comprising/consisting essentially of/consisting of an anti-microbial agent comprising comprising/consisting essentially of/consisting of the extract as defined herein, optionally in admixture with: one or more synergistic agent selected from the group of: anti-acne actives, anti-microbial actives, anti-fungal actives, anti-inflammatory actives, exfoliating agents and mixtures thereof; and a physiologically-acceptable carrier. In one embodiment, the anti-microbial agent comprises comprising/consists essentially of/consists of the extract as defined herein effective for inhibiting *P. acne* in a physiologically-acceptable carrier. By way of example, the composition may comprise/consist essentially of/consist of between 0.001% and 50% (w/w) active ingredients, and 50% to 99.999% (w/w) physiologically-acceptable carrier.

The compositions of the invention include those suitable for oral, nasal, mucosal, rectal, topical, buccal (e.g., sub-lingual), mucosal, intraperitoneal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound that is being used.

Compositions suitable for oral administration may be presented in discrete units, such as capsules, cachets, lozenges, or tablets, each containing a predetermined amount of the active compound; as a powder or granules; as a solution or a suspension in an aqueous or non-aqueous liquid or paste (such as gel, lotion, cream, ointment, etc.); or as an oil-in-water or water-in-oil emulsion. Such compositions may be prepared by any suitable method of pharmacy, which includes the step of bringing into association the active compound and a suitable carrier (which may contain one or more accessory ingredients as noted above).

Compositions suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Compositions of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes that render the composition isotonic with the blood of the intended recipient. Aqueous and non-aqueous sterile suspensions may include suspending agents and thickening agents. The compositions may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

For example, in one embodiment of the present invention, there is provided an injectable, stable, sterile composition comprising an active compound as described herein, or a salt or prodrug thereof, in a unit dosage form in a sealed container. The compound or salt is provided in the form of a lyophilisate that is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent that is physiologically acceptable may be employed in sufficient quantity to emulsify the compound or salt in an aqueous carrier. One such useful emulsifying agent is phosphatidylcholine.

Compositions suitable for rectal administration are preferably presented as unit dose suppositories. These may be prepared by mixing the active compound with one or more conventional solid carriers, for example, cocoa butter, and then shaping the resulting mixture.

In an alternative embodiment, the present composition may be administered via topical administration.

Compositions suitable for topical application to the skin preferably take the form of a semi-liquid of semi-solid formulation such as: ointment, cream, salve, foam, lotion, paste, gel, spray, aerosol, or oil. Carriers that may be used include petroleum jelly, lanoline, polyethylene glycols, alcohols (e.g., ethanol, isopropanol, etc.), transdermal enhancers, and combinations of two or more thereof.

Alternatively, the present composition may be formulated in a microcrystalline form, in a liposomal preparation or as a wipe. The present composition may be formulated to be used as a cleanser or a toner. The present composition may be formulated to be used on the whole surface of a target skin area or for spot skin treatment. Formulations suitable for a desired route of administration are within the skill of one in the art.

Inactive Ingredients and Carriers

The composition of the present invention may comprise, in addition to the active agent, one or more inactive ingredient selected from the group consisting of: carriers or excipients, viscosity or building agents, thickening agents, gelling agents and preservative agents.

The pharmaceutical compositions of the present invention can be formulated based on their routes of administration using methods well known in the art. For example, a sterile injectable preparation can be prepared as a sterile injectable aqueous or oleaginous suspension using suitable dispersing or wetting agents and suspending agents. Suppositories for rectal administration can be prepared by mixing drugs with a suitable non-irritating excipient such as cocoa butter or polyethylene glycols which are solid at ordinary temperatures but liquid at the rectal temperature and will therefore melt in the rectum and release the drugs. Solid dosage forms for oral administration can be capsules, tablets, pills, powders or granules. In such solid dosage forms, the active compounds can be admixed with at least one inert diluent such as sucrose lactose or starch. Solid dosage forms may also comprise other substances in addition to inert diluents, such as lubricating agents. In the case of capsules, tablets and pills, the dosage forms may also comprise buffering agents. Tablets and pills can additionally be prepared with enteric coatings. Liquid dosage forms for oral administration can include pharmaceutically acceptable emulsions, solutions, suspensions, syrups or elixirs containing inert diluents commonly used in the art. Liquid dosage forms may also comprise wetting, emulsifying, suspending, sweetening, flavoring, or perfuming agents. The pharmaceutical compositions of the present invention can also be administered in the form of liposomes, as described in U.S. Pat. No. 6,703,403. Formulation of drugs that are applicable to the present invention is generally discussed in, for example, Hoover, John E., REMINGTON'S PHARMACEUTICAL SCIENCES (Mack Publishing Co., Easton, Pa.: 1975), and Lachman, L., eds., PHARMACEUTICAL DOSAGE FORMS (Marcel Decker, New York, N.Y., 1980).

The choice of a suitable physiologically-acceptable carrier will depend on the exact nature of the particular formulation desired, e.g. whether the present topical composition is to be formulated into a liquid solution, a suspension, an ointment, a film or a gel. The choice of a suitable physiologically-acceptable carrier will also depend on the route of administration. Preferably, the carrier is formulated to be suitable for topical administration.

In accordance with a particular embodiment, the inactive ingredient may be: a polyacrylate, carbopol 940,934,970, 974, acacia, alginic acid, bentonite, carboxymethylcellulose, ethylcellulose, gelatin, hydroxyethylcellulose, hydroxypropyl cellulose, magnesium aluminum silicate, methylcellulose, poloxamers, polyvinyl alcohol, sodium alginate, tragacanth, and xanthan gum or mixtures thereof.

In still another embodiment, preservatives like paraben and triethanolamine may be added to increase the stability of the composition.

In the case of a topical formulation in a gel form, the carrier may be selected from the group consisting of: purified water; ammonium acryloyldimethyltaurate; VP colopolymer; aloe vera; edetate disodium; allantoin; methylchloroisothiazolinone; methyl isothiazolinone; and mixtures thereof.

Alternatively, the present composition may be formulated as an anti-bacterial soap or detergent, for preventive or hygienic purposes. Particularly, in one embodiment, the anti-microbial detergent comprises an extract of the present invention in combination with one or more additional cleaning composition components. The choice of additional components is within the skill of the artisan and includes conventional ingredients, including the exemplary non-limiting components set forth herein.

The detergent composition may be suitable for washing skin or mucus membranes (mouthwash, nose drops or rinse, etc.), or cleaning hard surfaces such as e.g. floors, tables, or dish wash.

Subject

In accordance with another embodiment, the mammal may be a human, a farm animal or a pet such as, for example, horses, rabbits, cats or dogs, particularly dogs.

Particularly, when treating a SA or MRSA infection, the mammal is a human.

Alternatively, when treating a SP or MRSP infection, the mammal is a pet such as, cats or dogs, particularly dogs.

Alternatively, when treating a SI or MRSI infection, the mammal is a farm animal such as horse or rabbit, particularly rabbit.

Alternatively, when treating acne, the mammal is a human.

Cosmetics Indications

The present invention also provides for a use or a method for alleviating acne-associated symptoms, the method comprises administering to a skin area affected by acne a therapeutically-effective amount of a composition comprising the extract directed against the organisms associated with acne and a physiologically-acceptable carrier, optionally in admixture with one of: anti-acne actives, anti-microbial actives, antifungal actives, anti-inflammatory actives, exfoliating agents and mixtures thereof. Compositions for alleviating acne-associated symptoms are disclosed herein.

The following examples are put forth so as to provide those of ordinary skill in the art with a complete disclosure and description of how to make and use the present invention and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

This disclosure describes seaweed harvesting, preparation of extracts, and testing for anti-microbial activity.

Example 1

Seaweed Collection and Identification

Seaweeds were collected by hand from Newfoundland or Labrador, Canada (Table 1). Samples were placed in plastic sampling bags and transported to Applicant's premises in coolers of seawater. Upon arrival in the laboratory, the specimens were washed individually to remove epiphytic and extraneous matter (sand, mussels, isopods, etc.). Samples were then checked visually to ensure they were clean. If not, remaining matter was removed by hand with further washing. Seaweeds were blotted dry, weighed to the nearest gram (plant wet weight) and shredded. The shredded material was transferred into Erlenmeyer flasks and frozen at $-60°$ C. until the extracts were prepared.

Figure 2:
FIG. 2. Photograph of *Polysiphonia urceloata*.
Figure 3:
FIG. 3. Photograph of *Cystoclonium purpureum*.
Figure 4:
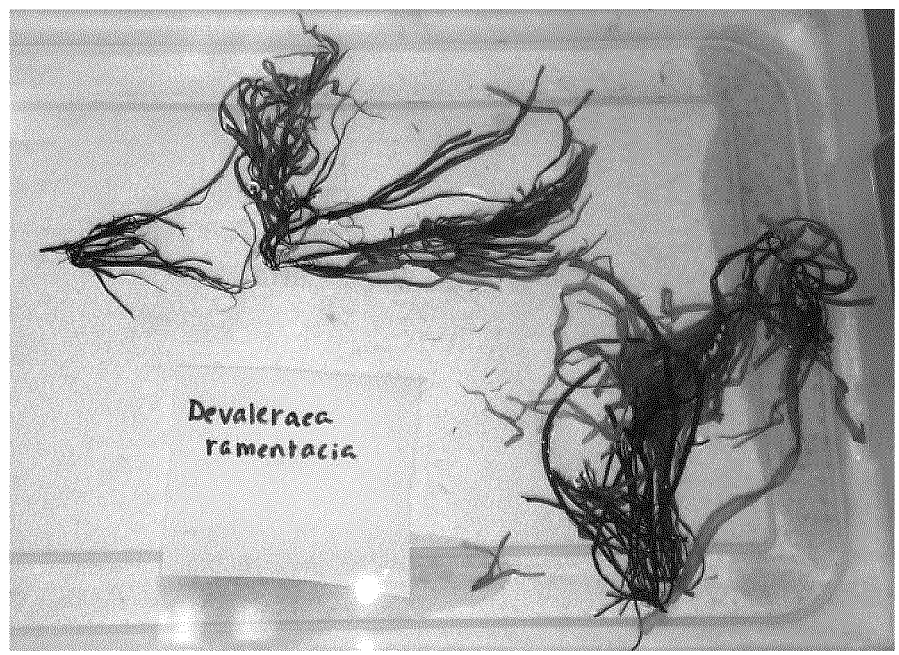
FIG. 4. Photograph of *Devaleraea ramentacia*.

A representative sample of each seaweed was photographed (FIGS. 1-4) and frozen at $-20°$ C. for confirmation of species by Dr. Robert Hooper, a phycologist at Memorial University of Newfoundland.

Preparation of Extracts

Preparation of extract involved freeze drying and defatting samples, followed by extraction with 80% aqueous ethanol.

Freeze-Drying

Seaweeds were freeze-dried prior to extraction. This step accounts for the differences in water content among seaweeds which may otherwise affect the solubility of bioactive components. Secondary plant metabolites are also more stable when stored in a dried form. Moreover, the large-scale extraction of dried plant material may cause fewer problems than extracting fresh material. In order to preserve thermolabile compounds, low temperature conditions are used throughout the process of extraction.

Erlenmeyer flasks containing the shredded seaweeds, which had been frozen at −60° C., were placed on a freeze-dryer, and lyophilized for 72-96 h at 69×10$^{-3}$ mbar. The weight (g) of dry material was then recorded.

Defatting of Samples

The lipid fraction of seaweed is known to vary from 1 to 5% of the algal dry matter, which can be dominated by polyunsaturated fatty acids. Brown and red seaweeds are particularly rich in long chain polyunsaturated fatty acids such as eicosapentaenoic acid (n3, C20:5), while green seaweeds may possess a level of alpha linoleic acid (n3, C18:3). Since these polyunsaturated fatty acids are extremely susceptible to oxidation, they may result in lipid oxidation products during analysis. In order to eliminate the above oxidative processes that may have an effect on the results, samples were defatted prior to extraction.

Freeze dried seaweed samples were ground into a powder and defatted by blending the powder with hexane (1:5, w/v, 5 min) in a Waring blender at ambient temperature. Defatted samples were air-dried, vacuum packed in polyethylene pouches and kept at 4° C. until extraction.

Example 2

Crude Extraction

Different solvents or solvent systems can be used for the extraction. In general, ethanol is commonly used due to its lower toxicity compared to other solvents. Moreover, ethanol extracts have been demonstrated in many studies to have the highest antioxidant activity.

In the current study, bioactive compounds were extracted into 80% aqueous ethanol at 4° C. for 24 h. The solvent was then removed under a vacuum at 37° C. for 45 to 60 min and the resulting concentrated slurries were lyophilized for 72 to 96 h at −80° C. and 69×10$^{-3}$ mbar using a freeze dryer. Dry extracts were weighed and stored at −60° C. until preparation for screening.

Extraction Yields

Extraction yields were calculated and expressed as g of dry extract per kg of dry seaweed. Twenty-five (25) mg of each extract was sent for anti-microbial screening assays.

TABLE 1

Extraction Yields

| # | Species | Date Collected | Location | Extract dry weight (g) | Yield (g of dry extract/g of dry plant) |
|---|---|---|---|---|---|
| 1 | Polysiphonia urceloata | Sep. 9, 2014 | Rocky harbour, NL | 0.91 | 1.88 |
| 2 | Devaleraea ramentacia | Jul. 29, 2015 | Pinware, Labrador | 0.22 | 1.54 |
| 4 | Cystoclonium purpureum | Aug. 2, 2015 | St. Paul's, NL | 0.23 | 0.67 |
| 7 | Polysiphonia lanosa | Aug. 3, 2015 | Rocky Harbour, NL | 1.35 | 2.33 |

Example 3. Anti-Microbial Screening of Seaweed Extracts

Study Design

Stock solutions of extracts were prepared in dimethylsulfoxide (DMSO) at 10 mg/ml and stored in 200 µl aliquots at −20° C. until used. Two pathological agents were assessed: resistant *Staphylococcus aureus* and resistant *Staphylococcus pseudointermedius*. Three concentrations of each extract (5, 10 and 25 µg/ml) were evaluated in triplicate for each trial. Vehicle alone served as negative control. Chloramphenicol (30 µg/ml) served as a positive control. For selected samples, studies were repeated at 100 and 50 µg/ml.

Liquid Phase Testing

A standard micro or mini-prep chase study was conducted. Briefly, liquid media was inoculated with a starting bolus of 0.01% bacteria and spiked with test extract at the study concentrations. Samples were incubated (shaking, 37° C.) overnight for 16 hours and bacterial growth enumerated by UV spectrometry in quadruplicate.

Solid Phase Testing

A standard zone occlusion study was conducted. Petri dishes containing solid agar were overlaid with soft agar spiked with each test bacteria and equidistant wells created in each plate. Test material was added to each well in triplicate and plates incubated overnight. Bacterial growth was enumerated by measuring the diameter of bacterial inhibition around each well.

Results

The results of the liquid phase testing are shown as mean optical density (OD) and fold change relative to vehicle controls in Table 2 and Table 3, respectively. *Polysiphonia lanosa* was further evaluated at 100 and 50 µg/ml in liquid phase with results detailed in Table 4.

TABLE 2

Liquid phase testing—OD$_{600}$

| | | S. aureus | | S. pseudo | | P. acnes | |
|---|---|---|---|---|---|---|---|
| # | Species | µg/ml | OD 600 | SD | OD 600 | SD | OD 600 | SD |
| 1 | Polysiphonia urceloata | 25 | 0.832 | 0.026 | 0.487 | 0.040 | 0.000 | 0.000 |
| | | 10 | 0.792 | 0.019 | 0.473 | 0.021 | 0.013 | 0.020 |
| | | 5 | 0.801 | 0.027 | 0.458 | 0.032 | 0.532 | 0.029 |
| 2 | Devaleraea ramentacia | 25 | 0.821 | 0.047 | 0.546 | 0.082 | 0.009 | 0.009 |
| | | 10 | 0.793 | 0.063 | 0.389 | 0.055 | 0.353 | 0.046 |
| | | 5 | 0.774 | 0.062 | 0.382 | 0.035 | 0.627 | 0.065 |
| 4 | Cystoclonium purpureum | 25 | 0.838 | 0.035 | 0.597 | 0.036 | 0.034 | 0.024 |
| | | 10 | 0.779 | 0.033 | 0.384 | 0.026 | 0.056 | 0.033 |
| | | 5 | 0.782 | 0.019 | 0.324 | 0.027 | 0.114 | 0.021 |
| 7 | Polysiphonia lanosa | 25 | 0.824 | 0.063 | 0.257 | 0.018 | 0.632 | 0.074 |
| | | 10 | 0.770 | 0.037 | 0.221 | 0.010 | 0.672 | 0.035 |
| | | 5 | 0.754 | 0.075 | 0.309 | 0.044 | 0.639 | 0.044 |
| Media | | 25 | 0.904 | 0.046 | 0.469 | 0.061 | 0.613 | 0.040 |
| | | 10 | 0.860 | 0.032 | 0.437 | 0.040 | 0.661 | 0.037 |
| | | 5 | 0.863 | 0.020 | 0.426 | 0.003 | 0.552 | 0.072 |
| CAP | | 30 | 0.023 | 0.029 | 0.021 | 0.024 | 0.005 | 0.008 |

Media: vehicle controls (DMSO);
CAP: Chloramphenicol treated

TABLE 3

Liquid phase testing—Fold Change

| | | | S. aureus | | S. pseudo | | P. acnes | |
|---|---|---|---|---|---|---|---|---|
| # | Species | µg/ml | Fold | Error | Fold | Error | Fold | Error |
| 1 | Polysiphonia urceloata | 25 | 0.92 | 0.03 | 1.04 | 0.08 | 0.00 | 0.00 |
| | | 10 | 0.92 | 0.02 | 1.08 | 0.05 | 0.02 | 0.03 |
| | | 5 | 0.93 | 0.03 | 1.07 | 0.08 | 0.88 | 0.05 |
| 2 | Devaleraea ramentacia | 25 | 0.91 | 0.05 | 1.16 | 0.18 | 0.01 | 0.01 |
| | | 10 | 0.92 | 0.07 | 0.89 | 0.13 | 0.58 | 0.08 |
| | | 5 | 0.90 | 0.07 | 0.90 | 0.08 | 1.03 | 0.11 |

TABLE 3-continued

Liquid phase testing—Fold Change

| | | | S. aureus | | S. pseudo | | P. acnes | |
|---|---|---|---|---|---|---|---|---|
| # | Species | μg/ml | Fold | Error | Fold | Error | Fold | Error |
| 4 | Cystoclonium | 25 | 0.93 | 0.04 | 1.27 | 0.08 | 0.06 | 0.04 |
| | purpureum | 10 | 0.91 | 0.04 | 0.88 | 0.06 | 0.09 | 0.05 |
| | | 5 | 0.91 | 0.02 | 0.76 | 0.06 | 0.19 | 0.03 |
| 7 | Polysiphonia | 25 | 0.91 | 0.07 | 0.55 | 0.04 | 1.04 | 0.12 |
| | lanosa | 10 | 0.89 | 0.04 | 0.51 | 0.02 | 1.10 | 0.06 |
| | | 5 | 0.87 | 0.09 | 0.73 | 0.10 | 1.05 | 0.07 |
| Media | | 25 | 1.00 | 0.05 | 1.00 | 0.13 | 1.00 | 0.07 |
| | | 10 | 1.00 | 0.04 | 1.00 | 0.09 | 1.00 | 0.06 |
| | | 5 | 1.00 | 0.02 | 1.00 | 0.01 | 1.00 | 0.12 |
| CAP | | 30 | 0.03 | 0.03 | 0.04 | 0.05 | 0.01 | 0.01 |

Media: vehicle controls (DMSO);
CAP: Chloramphenicol treated

TABLE 4

Liquid phase testing at higher concentration—$OD_{600}$

| | | | S. aureus | | S. pseudo | | P. acnes | |
|---|---|---|---|---|---|---|---|---|
| # | Species | μg/ml | OD600 | SD | OD600 | SD | OD600 | SD |
| 7 | Polysiphonia | 100 | 0.371 | 0.088 | 0.248 | 0.027 | 0.063 | 0.007 |
| | lanosa | 50 | 0.487 | 0.080 | 0.322 | 0.037 | 0.228 | 0.027 |
| Vehicle | | 1% | 0.730 | 0.013 | 0.533 | 0.050 | 0.514 | 0.052 |
| CAP | | 30 | 0.002 | 0.003 | 0.004 | 0.002 | 0.000 | 0.000 |

TABLE 5

Liquid phase testing at higher concentration—Fold change

| | | | S. aureus | | S. pseudo | | P. acnes | |
|---|---|---|---|---|---|---|---|---|
| # | Species | μg/ml | Fold | Error | Fold | Error | Fold | Error |
| 7 | Polysiphonia | 100 | 0.51 | 0.12 | 0.47 | 0.05 | 0.12 | 0.01 |
| | lanosa | 50 | 0.67 | 0.11 | 0.60 | 0.07 | 0.44 | 0.05 |
| Vehicle | | 1% | 1.00 | 0.02 | 1.00 | 0.09 | 1.00 | 0.10 |
| CAP | | 30 | 0.00 | 0.00 | 0.01 | 0.00 | 0.00 | 0.00 |

Vehicle: vehicle controls (DMSO);
CAP: Chloramphenicol treated;
—: no growth detected At 100 μg/ml, *Polysiphonia lanosa* inhibited MRSA growth by 50% and also inhibited resistant *Staphylococcus pseudintermedius* (MRSP) growth in liquid phase by approximately 50% at 10 μg/ml.

Numerous extracts inhibited *Propionibacterium acnes* growth, several completely stopping bacterial growth. Follow-up analyses confirmed that there was no contaminating influence and that all controls functioned as expected, suggesting that the results were accurate.

Testing samples at 100 μg/ml was complicated by the propensity for some samples to precipitate and artificially elevate $OD_{600}$ readings. This effect was compensated for as possible but accounts for some minor differences between effects observed under 50 μg/ml and effects observed above 50 μg/ml for some samples.

Summary

One extract was superior to other test extracts. *Polysiphonia lanosa* inhibited the growth of all three test pathogens in a dose-dependent study in liquid phase. The following is a summary of results for this extract: MRSA: 50% at 100 μg/ml; MRSP: 50% at 10 μg/ml; *P. acnes:* 50% at 50 μg/ml.

The invention claimed is:

1. A method for treating a microbial infection in a mammal comprising administering an effective amount of an aqueous ethanol extract of *Polysiphonia lanosa* (PL), wherein the microbial infection is a *Propionibacterium acnes* infection, a *Staphylococcus pseudintermedius* (SP) infection, or a methicillin-resistant *Staphylococcus pseudintermedius* (MRSP) infection.

2. The method of claim 1, wherein the extract of PL was extracted with between 25% and 90% aqueous ethanol.

3. The method of claim 2, wherein the extract of PL was extracted with 80% aqueous ethanol.

4. The method of claim 1, wherein the extract of PL is in dried form or is in solution.

5. The method of claim 1, wherein the mammal is a human or a pet.

6. The method of claim 1, comprising applying an effective amount of a topical formulation comprising the PL extract for the treatment of SP or MRSP in dogs.

7. The method of claim 6, wherein the topical formulation is paste, lotion, cream, gel, or ointment.

8. The method of claim 6, wherein said effective amount is a concentration between about 0.5 μg/ml to about 1000 μg/ml.

9. The method of claim 8, wherein said effective amount is a concentration between 50 μg/ml to 500 μg/ml.

* * * * *